(12) United States Patent
Bagrov et al.

(10) Patent No.: US 6,629,970 B2
(45) Date of Patent: Oct. 7, 2003

(54) METHOD OF RESTORING ENDOTHELIUM OF CORNEA

(75) Inventors: Sergei Nikolaevich Bagrov, Moscow (RU); Tamara Ilinichna Ronkina, Moscow (RU); Irina Alexandrovna Maklakova, Moscow (RU); Andrei Valentinovich Zolotorevsky, Moscow (RU)

(73) Assignee: Obschestvo S Ogranichennoi Otvetstvennostiju "Nauchno-Experimentalnoe Proizvodstvo Mikrokhirurgia Glaza", Moscow (RU)

( * ) Notice: Subject to any disclaimer, the term of this patent is extended or adjusted under 35 U.S.C. 154(b) by 0 days.

(21) Appl. No.: 09/897,953

(22) Filed: Jul. 5, 2001

(65) Prior Publication Data

US 2002/0017305 A1 Feb. 14, 2002

(30) Foreign Application Priority Data

Jul. 6, 2000 (RU) ......................................... 2000117605

(51) Int. Cl.⁷ .............................................. A61M 31/00
(52) U.S. Cl. ....................................... 604/521; 128/898
(58) Field of Search ................................. 604/500, 521, 604/27, 28, 294, 295; 424/93.43, 94.62, 78.02, 78.04, 423, 427, 428, 429; 623/4.1, 6.11; 128/898

(56) References Cited

U.S. PATENT DOCUMENTS 5,561,110 A * 10/1996 Michaelis et al. ............ 514/13
6,001,853 A * 12/1999 Zigler et al. ................ 514/315

FOREIGN PATENT DOCUMENTS

RU 2151580 6/2000
RU 2165749 4/2001

* cited by examiner

Primary Examiner—Brian L. Casler
Assistant Examiner—Jennifer Maynard
(74) Attorney, Agent, or Firm—Oblon, Spivak, McClelland, Maier & Neustadt, P.C.

(57) ABSTRACT

The invention relates to the field of medicine, in particular, to ophthalmology. The technical result of the invention is reduction of the loss of endothelium in the post-operation period, and during post-operation keratopathy and the initial stage of secondary endothelium-epithelium dystrophy—reduction of the edema and normalization of the thickness of the cornea. The technical result is achieved in that in a method of restoring the endothelium of the cornea, including administration of an activating solution into the anterior segment of the eye, in accordance with the invention, restoration of the endothelium of the cornea is effected with the aid of an activating solution having the following composition:

| | |
|---|---|
| carnosine | 0.1–20.0 mg |
| a complex of glycosaminoglycans with cations of at least one metal of the group consisting of calcium, magnesium, zinc, aluminum, copper, iron, manganese in 1 ml of a balanced salt solution. | 0.005–0.15 mg |

36 Claims, No Drawings

METHOD OF RESTORING ENDOTHELIUM OF CORNEA

FIELD OF THE INVENTION

The invention relates to the field of medicine, in particular, to ophthalmology.

BACKGROUND OF THE INVENTION

It is known that under normal physiological conditions, the mitotic capability of cornea endothelium is limited. Regeneration of the endothelium takes place, as a rule, as a result of hypertrophy and migration of endothelium cells. With age, there is a constant reduction of the number of endothelium cells, and any damage, including surgical trauma, increases the percentage of their loss. A reduction of the density of endothelium cells to below the critical level (less than 1000 cells per $mm^2$) results in the development of endothelium-epithelium dystrophy (EED) of the cornea, which means a sharp loss of eyesight and capability of working.

A method of restoring damaged endothelium is known, this method consisting in administering a purified fibroblastic growth factor into the anterior chamber of the eye (Exp. Eye Res., 1987, 45, 805–807). However, the author has only achieved favorable results in experiments.

A drawback of the proposed method is the necessity to introduce a substance of protein nature into the eye cavity, as a result of which an allergic reaction may occur.

The object of the invention is to create a safe and effective method of activating the proliferation of endothelium in order to reduce the loss of endothelium cells during surgical intervention, and also of restoring damaged endothelium of the cornea of a human during post-operation keratopathy and the development of secondary endothelium-epithelium dystrophy.

The technical result of the invention is reduction of the loss of endothelium in the post-operation period, and during post-operation keratopathy and the initial stage of secondary endothelium-epithelium dystrophy are reduction of the edema and normalization of the thickness of the cornea, increase of the density of the endothelium and disappearance of the feeling of discomfort in a patient as a result of activation of the proliferation of endothelium, normalization of the level of hydration and activation of metabolism in the tissue of the cornea, stabilization of cell membranes of the cornea and suppression of the processes of development of inflammation.

SUMMARY OF THE INVENTION

The technical result is achieved in that in a method of restoring the endothelium of the cornea, including administration of an activating solution into the anterior segment of the eye, in accordance with the invention, restoration of the endothelium of the cornea is effected with the aid of an activating solution having the following composition:

| | |
|---|---|
| carnosine | 0.1–20.0 mg |
| a complex of glycosaminoglycans with cations of at least one metal of the group consisting of calcium, magnesium, zinc, aluminum, copper, iron, manganese in 1 ml of a balanced salt solution, wherein the activating solution may additionally contain glycosaminoglycans in an amount of from 0.005 to 1.0 mg. | 0.005–0.15 mg | in 1 ml of a balanced salt solution, wherein the activating solution may additionally contain glycosaminoglycans in an amount of from 0.005 to 1.0 mg.

The balanced salt solution may be a 0.001–0.01 M phosphate buffer with pH=7.2–7.6 in a 0.14–0.16 M solution of sodium chloride.

DETAILED DESCRIPTION OF THE INVENTION

During extraction of a cataract with implantation of an intraocular lens (IOL) or during implantation of an IOL for refraction, the anterior chamber of the eye is filled with the activating solution after the operation is over, or irrigation with the activating solution in an amount of 20–200 ml is carried out during the whole operation.

In order to reduce the loss of the density of endothelium cells after the operation, the activating solution is administered subconjunctivally with 0.3 ml daily for 3–5 days.

In the case of keratopathy in the post-operation period or during the development of the initial stage of secondary EED, the activating solution is administered subconjunctivally with 0.3 ml daily for 5–10 days or by the phonophoresis method through the cornea in a continuous mode for 10 minutes at an intensity of 0.2–0.3 $W/cm^2$ with use of 5 ml of the solution daily, wherein 5–8 sessions are carried out.

The activating solution may additionally contain a viscoelastic in an amount of 90–99% by weight and the anterior chamber of the eye is filled with it at the initial stage of the operation.

The complex of glycosaminoglycans (GAGs) with cations of at least one metal from the group consisting of calcium, magnesium, zinc, aluminum, copper, iron, manganese, has a multifactor effect on the cornea of the eye. It is known that cations of metals, which are present in human tissues, activate many biochemical processes. In turn GAGs are inherent components of connective tissue, in particular of the cornea, and actively participate in water-salt metabolism, stimulate the reparation of damaged connective tissue by activating cellular elements, reduce inflammatory reaction. In the case of damage to the connective tissue, the concentration of GAGs in the damage zone is sharply reduced and the additional administration of GAGs promotes active restoration of normal tissue. By nature GAGs are polysaccharides, built from repeating disaccharide components which usually contain ammo sugar and uronic acid. Keratan sulfate, hondroitin sulfate, heparin, heparan sulfate, hyaluronic acid, dermatan sulfate relate to GAGs. All the GAGs are polyanions due to the presence in their structure of acid sulfate groups or carboxy groups of uronic acids.

The GAG complex with metal cations, which is prepared under conditions corresponding to physiological (osmomolarity and pH equal to those of tissue liquid), is an adequately natural carrier of cations which are necessary for activation of biochemical processes, in particular to increase the mobility of endothelium cells—a necessary composite part of the regeneration process.

Experiments, which we have conducted on the eyes of rabbits, have shown that the administration of a complex of GAGs with cations of metals into the anterior segment of the eye after a dosed trauma of the endothelium results in intensification of the proliferation of endothelium cells. During incubation of a donor cornea of a person with a dosed trauma of endothelium in a solution of a complex of GAGs with cations of metals, a substantial reduction of the area of the zone deprived of endothelium, the appearance of mitosis figures in cells were observed with the subsequent normalization of the density of endothelium cells in that zone, which indicates the presence of the process of proliferation of endothelium. The observed effect may be related to activation of the fibroblastic growth factor, which is contained in the descemetic membrane in an inactive form.

In order to prepare a complex of GAG with metal cations, it is most preferable to use heparin, including its low-molecular fractions (so-called low-molecular heparin) and GAGs separated from eye tissue, for example from the cornea or from a vitreous body. Wherein, a mixture of GAGs may be used with any weight ratios of concrete representatives of the class of GAGs.

The complex of GAGs with metal cations is prepared in the following manner. At least one of the water-soluble salts of metal cations (for example, calcium chloride, magnesium chloride, zinc sulfate, aluminum sulfate, copper sulfate, ferric chloride, manganese chloride) in an amount five times by weight in excess is added to a GAG solution with a concentration of from 0.5 to 20 mg/ml in a 0.15 M Tris-HCl buffer, pH 7.2–7.6, mixed and left at 4–8° C. for 24 hours. The complex of GAGs with cations of metals is separated by means of gelchromatography, freeing from the low-molecular impurities. The concentration of the prepared solution of the complex is measured spectrophotometrically at a wavelength of 535 nm with 1,9-dimethylene blue dye (Connective Tissue Research, 1982, v. 9, pp. 247–248). Then the components of the activating solution in the concentrations according to the claims are mixed.

Carnosine—a histidine-containing dipeptide, is in many tissues of mammals and is a polyfunctional biologically active compound. It is a natural antioxidant, buffer of protons, stabilizer of the hydrate and lipid phase of cellular membranes, promotes the activation and normalization of the metabolic processes. The introduction of carnosine into the makeup of the activating solution makes it possible to normalize and activate the exchange and metabolic processes in stroma cells of the cornea and endothelium and substantially speeds up the processes of restoring the endothelium of the cornea.

The limiting concentrations of the components of the activating solution provide activation of the proliferation and effective restoration of the endothelium of the cornea. At lower concentrations a noticeable activation of the proliferation of the endothelium is not observed, at higher concentrations suppression of the process of regeneration of the endothelium takes place.

Viscoelastics—these are viscous solutions of different substances, which are used in ophthalmosurgery to maintain the volume of the anterior chamber and for mechanical protection of the endothelium of the cornea against trauma during the operation. They are introduced into the anterior chamber of the eye at the initial stage of the operation and are removed at the final stage. At present solutions of derivatives of methyl cellulose-Occucoat, (Eye World, v. 2, No. 3, p. 62, 1997), Visiton (RF patent No. 2114587), sodium hyaluronate-Provisc, Healon (J. Cataract Refract Surg., 1998, 24, pp. 678–683) and others are used in surgical practice.

The method is carried out in the following manner.

During surgical interventions, accompanied by opening the anterior chamber of the eye, for example, extraction of cataracts or implantation of IOL, etc., the anterior chamber is filled with the activating solution at the final stage of the operation so that it would directly contact the endothelium of the cornea during the first post-operation hours, gradually being replaced by the patient's secreted chamber moisture. During similar surgical interventions, irrigation of the anterior chamber may be effected with the activating solution during the whole operation period.

When the same surgical interventions are performed with an activating solution additionally containing viscoelastic, the anterior chamber is filled with this solution at the initial stage of the operation instead of with traditionally used viscoelastics. At the final stage of the operation the aforesaid activating solution is removed from the anterior chamber.

In order to reduce the loss of endothelium cells in the early post-operation period after extraction of the cataract, implantation of IOL, etc., a course of subconjunctive injections of the activating solution is carried out after the operation with a daily dose of 0.3 ml for 3–5 days.

In cases of post-operation keratopathy or the initial stage of endothelium-epithelium dystrophy of the cornea, the activating solution is administered subconjunctivally with a daily dose of 0.3 ml during 5–10 days. In similar cases the activating solution may be administered by phonophoresis. In order to do this 5 ml of the solution are placed in a phoretic bath placed on the cornea and phonophoresis is carried out in a continuous mode during 10 minutes at an intensity of 0.2–0.3 $W/cm^2$. Phonophoresis is carried out daily for 5–8 days.

EXAMPLES

Example 1

Female patient A., 65 years old, diagnosis—immature complicated cataract of the left eye. Density of endothelium cells (DEC)-2600 cells per $mm^2$. Extraction of cataract carried out using the phacoemulsification method with implantation of IOL. At the end of the operation 0.3 ml of an activating solution was administered into the anterior chamber. The composition of the solution was: a complex of keratan sulfate and hondroitin sulfate with cations of bivalent manganese—0.005 mg, carnosine—20 mg, in 1 ml of a balanced salt solution. After 6 months the DEC was 2400–2500 cells per $mm^2$. The loss of DEC was 5.8%, while the average loss of DEC when a similar operation is carried out without use of the activating solution is 10.6%.

Example 2

Female patient K., 70 years old, diagnosis—mature senile cataract of the left eye, DEC—2500–2700 cells per $mm^2$. Extracapsular extraction of cataract carried out with implantation of IOL. After the end of the operation 0.3 ml of an activating solution was subconjunctivally administered daily for 3 days. The composition of the solution was: a complex of heparin with magnesium cations—0.15 mg, carnosine—0.1 mg, in 1 ml of a balanced salt solution. After six months the loss of DEC was 5%, while the average loss of DEC when similar operations are carried out without use of the activating solution is 12.3%.

Example 3

Male patient B., 65 years old, diagnosis—immature senile cataract of the left eye. DEC—2700–2900 cells per $mm^2$. Extraction of cataract carried out using the phacoemulsification method with implantation of IOL. An activating solution of the following composition was used during the operation at the stages of carrying out capsulorexis, phacofragmentation of the core, aspiration-irrigation of the lenticular masses and washing out the viscoelastic: a complex of keratan sulfate with copper cations—0.05 mg, carnosine—1.0 mg, heparin—0.2 mg, in 1 ml of a balanced salt solution. One month after the operation DEC was 2600–2700 cells per mm$^2$, after 6 months DEC was without change. The loss of DEC was 7.1% while the average loss of DEC when similar operations are carried out without use of the activating solution is 13.7%.

Example 4

Female patient O., 72 years old, diagnosis—1st degree secondary endothelium-epithelium dystrophy of the cornea, DEC—700–800 cells per mm$^2$, thickness of the cornea in the central optical zone—607 μm. Course of conservative treatment carried out, including daily phonophoresis of the cornea during 5 days with the use of an activating solution of the following composition: carnosine—0.1 mg, a complex of keratan sulfate with copper cations—0.15 mg and hondroitin sulfate—0.005 mg, in 1 ml of a balanced salt solution. In order to carry out phonophoresis, 5 ml of an activated solution of the aforesaid composition was placed in a phoretic bath and phonophoresis was carried out in a continuous mode for 10 minutes at an intensity of 0.2–0.3 W/cm$^2$. One month after treatment, DEC—1000–1100 cells per mm$^2$, after 3 months after treatment-800–1000. Another course of phonophoresis was carried out, after which DEC increased to 900–1000 cells per mm$^2$ and remained stable for 1 year. The thickness of the cornea in the central optical zone of the cornea after treatment decreased to 534 μm.

Example 5

Female patient T., 71 years old, diagnosis—mature cataract of the right eye. DEC—1800–2000 cells per mm. Extracapsular extraction of the cataract carried out with implantation of IOL. A solution, additionally containing viscoelastic on the base of water-soluble derivatives of cellulose, of the following composition was used as the activating solution: a complex of hyaluronic acid with iron cations—0.05 mg, carnosine—0.1 mg, sodium hyaluronate—1.0 mg and viscoelastic—0.9 mg, in 1 ml of a balanced salt solution. After 1 month after the operation, DEC-1700–1900 cells per mm$^2$, after 3 months DEC did not change. The loss of DEC was 5.5%, while the average loss of DEC when similar operations are carried out without using the activating solution is 11.6%.

What is claimed is:

1. A method of restoring the endothelium of the cornea by administering an activating solution into the anterior segment of the eye, wherein the activating solution comprises carnosine and a complex of glycosaminoglycans with cations of at least one metal of the group consisting of calcium, magnesium, zinc, aluminum, copper, iron, manganese, with the following ratio of the components in 1 ml of a balanced salt solution

| | |
|---|---|
| carnosine | 0.1–20.0 mg |
| a complex of glycosaminoglycans with cations of at least one metal of the group consisting of calcium, magnesium, zinc, aluminum, copper, iron, manganese. | 0.005–0.15 mg |

2. The method according to claim 1, wherein the activating solution further comprises glycosaminoglycans in an amount of from 0.005 to 1.0 mg.

3. The method according to claim 1 wherein a 0.001–0.01 M phosphate buffer with a pH of 7.2–7.6 in a 0.14–0.16 M solution of sodium chloride is used as the balanced salt solution.

4. The method according to claim 1, wherein the activating solution is administered during an extraction of a cataract with implantation of an intraocular lens (IOL) for refraction or during implantation of an intraocular lens (IOL), and wherein the anterior chamber of the eye is filled with the activating solution after the extraction and implantation, or the eye is irrigated with the activating solution in an amount of 20–200 ml during the extraction and implantation.

5. The method according to claim 1, wherein to reduce the loss of endothelium cells after an operation, the activating solution is administered subconjunctivally in an amount of 0.3 ml daily for 3–5 days.

6. The method according to claim 1, wherein the activating solution is administered subconjunctivally in the eye, in an amount of 0.3 ml daily for 5–10 days or by phonophoresis through the cornea in a continuous mode for 10 minutes at an intensity of 0.2–0.3 W/cm$^2$ with use of 5 ml of the solution daily.

7. The method according to claim 1, wherein at an initial stage of an ocular operation the anterior chamber of the eye is filled with an activating solution further comprising a viscoelastic in an amount of 90–99% by weight.

8. The method according to claim 2, wherein the activating solution is administered during an extraction of a cataract with implantation of an intraocular lens (IOL) or during implantation of an intraocular lens (IOL) for refraction, and wherein the anterior chamber of the eye is filled with the activating solution after the extraction and implantation, or the eye is irrigated with the activating solution in an amount of 20–200 ml is carried out during the extraction and implantation.

9. The method according to claim 3, wherein the activating solution is administered during an extraction of a cataract with implantation of an intraocular lens (IOL) or during implantation of an intraocular lens (IOL) for refraction, and wherein the anterior chamber of the eye is filled with the activating solution after the extraction and implantation, or the eye is irrigated with the activating solution in an amount of 20–200 ml during the extraction and implantation.

10. The method according to claim 2, wherein to reduce the loss of endothelium cells after an operation, the activating solution is administered subconjunctivally in an amount of 0.3 ml daily for 3–5 days.

11. The method according to claim 3, wherein to reduce the loss of endothelium cells after an operation, the activating solution is administered subconjunctivally in an amount of 0.3 ml daily for 3–5 days.

12. The method according to claim 6, wherein the eye is keratopathic.

13. The method according to claim 6, wherein the activating solution is administered by phonophoresis and the administration is repeated 5 to 8 times.

14. The method according to claim 2, wherein the activating solution is administered subconjunctivally in the eye, in an amount of 0.3 ml daily for 5–10 days or by phonophoresis through the cornea in a continuous mode for 10 minutes at an intensity of 0.2–0.3 W/cm$^2$ with use of 5 ml of the solution daily.

15. The method according to claim 14, wherein the eye is keratopathic.

16. The method according to claim 15, wherein the activating solution is administered by phonophoresis and the administration is repeated 5 to 8 times.

17. The method according to claim 3, wherein the activating solution is administered subconjunctivally in the eye, in an amount of 0.3 ml daily for 5–10 days or by phonophoresis through the cornea in a continuous mode for 10 minutes at an intensity of 0.2–0.3 W/cm with use of 5 ml of the solution daily.

18. The method according to claim 17, wherein the eye is keratopathic.

19. The method according to claim 17, wherein the activating solution is administered by phonophoresis and the administration is repeated 5 to 8 times.

20. The method according to claim 1, wherein the activating solution is administered subconjunctivally in the eye, and the eye is developing secondary endothelium-epithelium dystrophy, in an amount of 0.3 ml daily for 5–10 days or by phonophoresis through the cornea in a continuous mode for 10 minutes at an intensity of 0.2–0.3 W/cm$^2$ with use of 5 ml of the solution daily.

21. The method according to claim 20, wherein the activating solution is administered by phonophoresis and the administration is repeated 5 to 8 times.

22. The method according to claim 2, wherein the activating solution is administered subconjunctivally in the eye, and the eye is developing secondary endothelium-epithelium dystrophy, in an amount of 0.3 ml daily for 5–10 days or by phonophoresis through the cornea in a continuous mode for 10 minutes at an intensity of 0.2–0.3 W/cm$^2$ with use of 5 ml of the solution daily.

23. The method according to claim 22, wherein the activating solution is administered by phonophoresis and the administration is repeated 5 to 8 times.

24. The method according to claim 3, wherein the activating solution is administered subconjunctivally in the eye, and the eye is developing secondary endothelium-epithelium dystrophy, in an amount of 0.3 ml daily for 5–10 days or by phonophoresis through the cornea in a continuous mode for 10 minutes at an intensity of 0.2–0.3 W/cm$^2$ with use of 5 ml of the solution daily.

25. The method according to claim 24, wherein the activating solution is administered by phonophoresis and the administration is repeated 5 to 8 times.

26. The method according to claim 2, wherein a 0.001–0.01 M phosphate buffer with a pH of 7.2–7.6 in a 0.14–0.16 M solution of sodium chloride is used as the balanced salt solution.

27. The method according to claim 2, wherein at an initial stage of an ocular operation the anterior chamber of the eye is filled with an activating solution further comprising a viscoelastic in an amount of 90–99% by weight.

28. The method according to claim 3, wherein at an initial stage of an ocular operation the anterior chamber of the eye is filled with an activating solution further comprising a viscoelastic in an amount of 90–99% by weight.

29. The method according to claim 26, wherein the activating solution is administered during an extraction of a cataract with implantation of an intraocular lens (IOL) for refraction or during implantation of an intraocular lens (IOL), and wherein the anterior chamber of the eye is filled with the activating solution after the extraction and implantation, or the eye is irrigated with the activating solution in an amount of 20–200 ml during the extraction and implantation.

30. The method according to claim 26, wherein to reduce the loss of endothelium cells after an operation, the activating solution is administered subconjunctively in an amount of 0.3 ml daily for 3–5 days.

31. The method according to claim 26, wherein the activating solution is administered subconjunctivally in the eye, in an amount of 0.3 ml daily for 5–10 days or by phonophoresis through the cornea in a continuous mode for 10 minutes at an intensity of 0.2–0.3 W/cm$^2$ with use of 5 ml of the solution daily.

32. The method according to claim 26, wherein at an initial stage of an ocular operation the anterior chamber of the eye is filled with an activating solution further comprising a viscoelastic in an amount of 90–99% by weight.

33. The method according to claim 31, wherein the eye is keratopathic.

34. The method according to claim 31, wherein the activating solution is administered by phonophoresis and the administration is repeated 5 to 8 times.

35. The method according to claim 26, wherein the activating solution is administered subconjunctivally in the eye, and the eye is developing secondary endothelium-epithelium dystrophy, in an amount of 0.3 ml daily for 5–10 days or by phonophoresis through the cornea in a continuous mode for 10 minutes at an intensity of 0.2–0.3 W/cm$^2$ with use of 5 ml of the solution daily.

36. The method according to claim 35, wherein the activating solution is administered by phonophoresis and the administration is repeated 5 to 8 times.

* * * * *